US00PP10386P

United States Patent [19]

Zaiger et al.

[11] Patent Number: Plant 10,386

[45] Date of Patent: May 12, 1998

[54] INTERSPECIFIC TREE "GEO PRIDE"

[76] Inventors: Chris Floyd Zaiger, 929 Grimes Ave.; Gary Neil Zaiger, 1907 Elm Ave.; Leith Marie Gardner, 1207 Grimes Ave.; Grant Gene Zaiger, 4005 California Ave., all of Modesto, Calif. 95358

[21] Appl. No.: 800,718

[22] Filed: Feb. 13, 1997

[51] Int. Cl.[6] ..... A01H 5/00

[52] U.S. Cl. ..... Plt./38.1

[58] Field of Search ..... Plt./38.1

*Primary Examiner*—James R. Feyrer

[57] ABSTRACT

A new and distinct interspecific tree (*Prunus salicina*× *Prunus armeniaca*) which has the following unique combination of desirable features that are outstanding in a new variety:

1. Regular and heavy production of fruit.
2. Fruit with firm flesh, good handling and shipping quality.
3. Fruit holding firm on the tree 10 to 12 days after maturity (shipping ripe).
4. Fruit with excellent flavor and eating quality.
5. Fruit with high soluble solids (Brix) averaging approximately 18° with the refractometer.
6. Relatively uniform ripening of fruit throughout the tree.
7. Vigorous, semi-upright growth of the tree.

1 Drawing Sheet

ORIGIN OF THE VARIETY

The new and distinct variety of interspecific tree was originated by us in our experimental orchard located near Modesto, Calif., as a first generation cross between two selected seedlings with field identification numbers 29EB30 and 42GA580. The maternal parent (29EB30) originated from a cross between Mariposa Plum (U.S. Plant Pat. No. 111) and a selected plum-cot seedling which originated from an open pollinated Red Beaut Plum (U.S. Plant Pat. No. 2,539) seed. The paternal parent (42GA580) is a plum-cot selection which originated as a seedling from seed of an open pollinated Red Beaut Plum tree that had been grown from budwood which had been irradiated with cobalt. The present new variety was selected from a large group of seedlings, which were grown and maintained by us, one such seedling having especially desirable fruit characteristics was selected for asexual reproduction and commercialization.

ASEXUAL REPRODUCTION OF THE VARIETY

Asexual reproduction of the new and distinct variety of interspecific tree was by budding, as performed by us in our experimental orchard located near Modesto, Calif., and shows that all characteristics of the tree and its fruit run true to the original tree and are established and transmitted through succeeding asexual propagations.

SUMMARY OF THE VARIETY

A new and distinct variety of interspecific tree which is of large size, vigorous, semi-upright growth and a regular and productive bearer of medium size, freestone fruit with excellent flavor and eating quality. The fruit is further characterized by having a distinctive sweet flavor, blending between apricot and plum, having a good balance between sugar and acid, also having a high soluble solids (Brix) of approximately 18%. The firm flesh of the fruit gives good handling and shipping quality, holding firm on the tree 10 to 12 days after maturity (shipping ripe). In comparison to the interspecific tree Flavor King (U.S. Plant Pat. No. 8,026). The fruit of the new variety is approximately 21 days earlier in maturity.

PHOTOGRAPH OF THE VARIETY

The accompanying color photographic illustration shows typical specimens of the foliage and fruit of the present new interspecific variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of interspecific tree, its flowers, foliage and fruit, as based on observations of specimens grown near Modesto, Calif., with color terminology (except those in common terms) in accordance with Reinhold Color Atlas by A. Kornerup and J. H. Wanscher.

Tree:
- *Size.*—Large.
- *Vigor.*—Vigorous.
- *Productivity.*—Productive.
- *Bearer.*—Regular.
- *Density.*—Medium.
- *Growth.*—Semi-upright.

Trunk:
- *Size.*—Medium to large.
- *Texture.*—Shaggy.
- *Color.*—Brown to tobacco brown (5-F-4) to (5-F-8).

Branches:
- *Size.*—Medium.
- *Texture.*—Medium rough.
- *Lenticels.*—Medium number. Large size.
- *Color.*—Hair brown to linoleum brown (5-E-4) to (5-E-7).

Leaves:
- *Size.*—Large. Average length 5". Average width 1⅞".
- *Form.*—Oblanceolate.
- *Margin.*—Serrulate.
- *Thickness.*—Medium.
- *Surface.*—Smooth.
- *Petiole.*—Long. Average length 1⅛". Average width 1/16".

*Glands.*—Globose. Number varies from 0 to 3. Average number 2. Small size. Located on upper portion of petiole and lower portion of leaf blade.

*Color.*—Upper surface — green to dark green (27-F-6) to (27-F-8). Lower surface — light green to pastel green (27-D-4) to (27-D-5).

Flower buds:

*Size.*—Medium.

*Length.*—Medium.

*Form.*—Plump.

Flowers:

*Size.*—Large.

*Pollen.*—Present.

*Blooming period.*—Date of first bloom: Feb. 21, 1996. Date of full bloom: Feb. 27, 1996. Varies slightly with climatic conditions.

*Color.*—White.

Fruit:

*Maturity when described.*—Firm ripe.

*Date of first picking.*—Jul. 15, 1996.

*Date of last picking.*—Jul. 21, 1996. Varies slightly with climatic conditions.

*Size.*—Medium. Average diameter axially 2". Average transversely in suture plane 2⅛".

*Form.*—Nearly globose, slightly flattened at apex and base.

*Suture.*—Shallow, extends from base to apex.

*Ventral surface.*—Nearly rounded, only slightly lipped.

*Apex.*—Slightly retuse.

*Base.*—Retuse.

*Cavity.*—Rounded to very slightly elongated in suture plane. Average depth ¼". Average breadth ⅜".

Flesh:

*Ripens.*—Evenly.

*Texture.*—Firm.

*Fibers.*—Few, small, tender.

*Aroma.*—Very slight.

*Amygdalin.*—Undetected.

*Eating quality.*—Excellent, mild, sweet, good balance between sugar and acid.

*Flavor.*—Excellent.

*Color.*—Light yellow (4-A-4) near pit cavity, color increases toward surface becoming darker yellow (5-A-5) to pastel red (10-A-4) near skin. Pit cavity — caramel (6-C-6).

Skin:

*Thickness.*—Medium.

*Texture.*—Medium, tenacious to flesh.

*Down.*—Wanting.

*Tendency to crack.*—Slight, next to stem.

*Color.*—Light yellow to yellow ground color (4-A-4) to (4-A-5). Overspread with garnet red to oxblood red (9-D-8) to (9-E-7), except in very small randomly spaced areas exposing a speckling of yellow ground color.

Stone:

*Type.*—Freestone.

*Size.*—Small. Average length ¾". Average width ⅝". Average thickness 7/16".

*Form.*—Obovoid.

*Base.*—Usually straight, varies from straight to rounded.

*Apex.*—Usually rounded, varies from rounded to slight tip.

*Surface.*—Slightly pitted throughout.

*Ridges.*—Shallow narrow ridges extending toward apex, ridges vary in height and length.

*Sides.*—Equal to unequal.

*Tendency to split.*—None.

*Color.*—Light tan to light brown. (5-B-5) to (5-C-5).

Use: Dessert. Market, local and long distance. Drying.

Keeping quality: Good.

Shipping quality: Good.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

We claim:

1. A new and distinct variety of interspecific tree, substantially as illustrated and described, characterized by its large size, vigorous, semi-upright growth and a productive and regular bearer of medium size, firm, freestone fruit; the fruit is further characterized by having a good balance between sugar and acid, excellent flavor and eating quality, good handling and shipping quality and, in comparison to the interspecific tree Flavor King (U.S. Plant Pat. No. 8,026), the fruit of the new variety is approximately 21 days earlier in maturity.

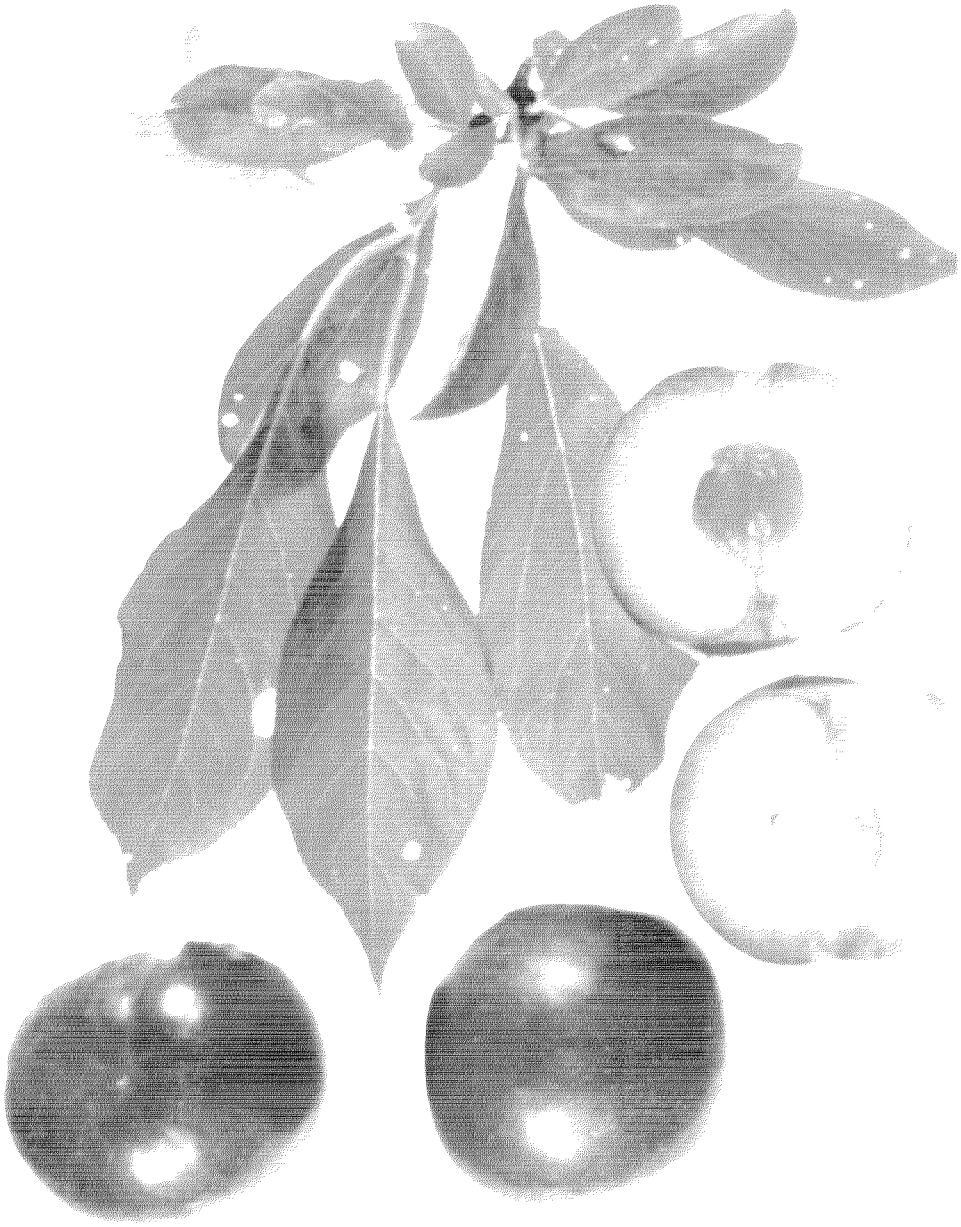

* * * * *